US006767712B2

(12) United States Patent
Prusiner et al.

(10) Patent No.: US 6,767,712 B2
(45) Date of Patent: Jul. 27, 2004

(54) MODELS OF PRION DISEASE

(75) Inventors: Stanley B. Prusiner, San Francisco, CA (US); Carsten Korth, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 17 days.

(21) Appl. No.: 09/895,963

(22) Filed: Jun. 28, 2001

(65) Prior Publication Data

US 2002/0004938 A1 Jan. 10, 2002

Related U.S. Application Data

(63) Continuation of application No. 09/318,888, filed on May 26, 1999, now abandoned.

(51) Int. Cl.$^{7}$ ........................ G01N 33/574; C12N 5/00; C12N 15/63

(52) U.S. Cl. ...................... 435/7.23; 435/325; 435/455; 435/320.1

(58) Field of Search ................................ 435/7.23, 455, 435/325, 375, 7.2, 320.1

(56) References Cited

U.S. PATENT DOCUMENTS

| | | | |
|---|---|---|---|
| 5,792,901 A | | 8/1998 | Prusiner et al. |
| 2002/0127583 A1 | * | 9/2002 | Hammond et al. |

OTHER PUBLICATIONS

Lahman et al. The Journal of Biological Chemistry 270:24589–24597, 1995.*

Lehaman et al.The Journal of Biological Chemistry, 272:21479–21487, 1997.*

Chabry et al. The Journal of Biological Chemistry 273:13203–13207, 1997.*

Aguzzi, A., et al., *Nature*, 389:795–798 (1997).

Alpers, M.P., *Slow Transmissible Diseases of the Nervous System*, vol. 1, S.B. Prusiner and W.J. Hadlow, eds. (New York: Academic Press), pp. 66–90 (1979).

Basler et al., "Scrapie and Cellular PrP Isoforms Are Encoded by the Same Chromosomal Gene," *Cell*, (Aug. 1, 1989), 46:417–28.

Billeter, et al., "Prion Protein NMR Structure and Species Barrier for Prion Diseases," *Proc. Natl. Acad. Sci. USA* (Jul. 1997), 94:7281–7285.

Bolton et al., "Identification of a Protein That Purifies with the Scrapie Prion," *Science* (Dec. 24, 1982) 218:1309–11 (1982).

Brown et al., "Friendly Fire "in Medicine: Hormones, Homografts, and Creutzfeldt–Jakob Disease, *Lancet* (Jul. 4, 1992)340:24–27.

Chazot, et al., "New Variant of Creutzfeldt–Jakob disease in a 2–year–old French Man," *Lancet* (Apr. 27, 1996) 347(9009):1181.

DeArmond et al., "Selective Neuronal Targeting in Prion Disease," *Neruon*, (Dec. 1997), 19:1337–1348.

Donne et al., "Structure of the Recombinant Full–Length Hamster Prion Protein PrP (29–231): The N Terminus is Highly Flexible," *Proc. Natl. Acad. Sci. USA* (Dec. 1997) 94:13452–13457.

Gajdusek et al., "Experimental Transmission of a Kuru–Like Syndrome to Chimpanzees," *Nature* (Feb. 1966) 209(5025):794–796.

GajAMsek, "Unconventional Viruses and the Origin and Disappearance of Kuru" *Science* (Sep. 2, 1977), 197(43):943–960.

Gibbs, Jr., et al., "Creutzfeldt–Jakob Disease (Spongiform Encephalopathy): Transmission to the Chimpanzee," ■*cience* (Jul. 1968), 161:388–389.

Gibbs, Jr., et al., "Strain Variation in the Viruses of Creutzfeldt–Jakob Disease and Kuru," *Slow Transmissible Diseases of the Nervous System*, vol. 2, S.B. Prusiner and W.J. Hadlow, eds. (New York: Academic Press), pp. 87–110 (1979).

Goldfarb et al., Fatal Familial Insomnia and Familial Creutzfeldt–Jakob Disease: Disease Phenotype Determined by a DNA Polymorphism, *Science*, (Oct. 30, 1992) 258:806–808.

Hadlow, "Scrapie and Kuru," *Lancet* (Sep. 5, 1959), 2:289–290.

Harries–Jones et al., "Creutzfeldt–Jakob Disease in England and Wales, 1980–1984: a Case–Control Study of Potential Risk Factors," *J. Neurol. Neurosurg. Psychiatry* (1988) 51:1113–1119.

Hsiao et al., "Inherited Human Prion Diseases," *Neurology* (Dec. 1990), 40:1820–1827.

James et al., "Solution Structure of a 142–Residue Recombinant Prion Protein Corresponding to the Infectious Fragment of the Scrapie Isoform," *Proc. Natl. Acad. Sci. USA* (Sep. 1997), 94:10086–10091.

Kitamoto et al., "Human Prion Diseases With Variant Prin Protein," *Phil. Trans. R. Soc. Lond. B*, (1994) 343:391–398.

Klatzo et al., "Pathology of Kuru," *Laboratory Investigation*, (Jul./Aug. 1959) 8(4):799–847.

(List continued on next page.)

*Primary Examiner*—Ram R. Shukla
(74) *Attorney, Agent, or Firm*—Karl Bozicevic; Bozicevic, Field & Francis LLP

(57) ABSTRACT

The present invention provides a novel PrP protein, and nucleic acids encoding this protein, where the PrP protein is characterized in vivo by 1) incomplete glycosylation relative to glycosylation of wild-type $PrP^{C}$ and 2) proper cellular localization, i.e. an ability to be transported to the cell surface. This novel, under-glycosylated PrP, unlike its normal cellular counterpart, can easily be converted into a protease-resistant isoform by incubation with infectious prions. The invention further provides systems for the study of prion disorders and methods of using these systems, e.g. the study of the mechanical processes in progression of prion-mediated disease or the identification of new therapeutic agents for treatment of prion-mediated disorders. In such systems, protease-resistant under-glycosylated PrP is generated de novo and can be detected by standard immunoblot techniques.

1 Claim, No Drawings-

OTHER PUBLICATIONS

McKinley et al., "A Protease–Resistant Protein Is a Structural Component of the Scrapie Prion," *Cell* (Nov. 1983) 35:57–62.

Kocisko et al. (Apr. 1995), "Species Specificity in the Cell–Free Conversion of Prion Protein Protease–Resistant Forms: A Model for the Scrapie Species Barrier." *Proc. Natl. Acad. Sci. USA*, vol. 92:3923–3927.

Lehmann et al. (1997), "Blockade of Glycosylation Promotes Acquisition of Scrapie–Like Properties by the Prion Protein Cultured Cells." *Journal of Biological Chemistry*, vol. 272(34):21479–21487.

Medori et al., Fatal Familial Insomnia, A Prion Disease With a Mutation at Codon 178 of The Prion Protein Gene, *New England Journal of Medicine*, ( Feb. 13, 1992), 326(7):444–449.

Peretz et al., "A Conformational Transition at the N–terminus of the Prion Protein Features in Formation of the Scrapie Isoform," *Journal of Molecular Biology*, (1997). 273:614–622.

Prusiner et al., "Further Purification and Characterization of ScrapiePrions," *Biochemistry* (1982), 21(26):6942–50.

Prusiner, et al., "Purification and Structural Studies of a Major Scrapie Prion Protein," *Cell* (Aug. 1984), 38:127–134.

Prusiner, "Molecular Biology of Prion Disease," *Science* (Jun. 14, 1991), 252:1515–1522.

Rogers, et al., "Conversion of Truncated and Elongated Prion Proteins into the Scrapie Isoform in Cultured Cells," *Proc. Natl. Acad. Sci. USA* (Apr. 1993), 90:3182–3186.

Saborio et al. (1999), "Cell–Lysate Conversion of Prion Protein into Its Protease–Resistant Isoform Suggest the Participation of a Cellular Chaperone." *Biochemical and Biophysical Research Communications*, vol. 258:470–475.

Taraboulos et al., "Acquisition of Protease Resistance by Prion Proteins in Scrapie–Infected Cells Does not Require Asparagine–linked Glycosylation." *Proc. Natl. Acad. Sci. USA*, (Nov. 1990) 87:8262–8266.

Tateishi et al., "Prion Protein Gene Analysis and Transmission Studies of Creutzfeldt–Jakob Disease,", *Prion Diseases of Humans and Animals*, Prusiner et al., (London: Ellis Horwood), (1992) pp. 129–134.

Telling, et al., Prion Propagaton in Mice Expressing Human and Chimeric PrP Transgenes Implicates the Interaction of Cellular PrP with Another Protein, *Cell* (Oct. 6, 1995), 83:79–90.

Telling et al., "Evidence for the Conformation of the Pathologic Isoform of the Prion Protein Enciphering and Propagating Prion Diversity,"*Science* (Dec. 20, 1996), 274:2079–2082.

Wilesmith, et al., "Bovine Spongiform Encephalopathy," *Current Topics in Microbiology and Immunology*, (1991) 172:21–38.

Will, et al., "A New Variant of Creutzfeldt–Jakob Disease in the UK,"*Lancet* (Apr. 6, 1996), 347:921–925.

Korth et al., "Expression of unglycosylated mutated prion protein facilitates $PrP^{Sc}$ formation in neuroblastoma cells infected with different prion strains," *J. Gen. Virol.* 81:2555–2563 (2000).

Prusiner, Stanley B., "Prions" *Proc. Natl. Acad. Sci. USA* 95:13363–13383 (Nov. 1998).

* cited by examiner

MODELS OF PRION DISEASE

CROSS-REFERENCES

This application is a continuation of earlier filed application Ser. No. 09/318,888 filed May 26, 1999 now abandoned which application is incorporated herein in its entirety and to which application is claimed priority under 35 U.S.C. §120.

GOVERNMENT RIGHTS

The United States Government may have certain rights in this application pursuant to Grant No. AG10770 awarded by the National Institutes of Health.

FIELD OF THE INVENTION

The present invention relates generally to systems for studying neurodegenerative disorders, and in particular to systems for the study of prion-associated disease.

BACKGROUND OF THE INVENTION

Prions are infectious pathogens that cause central nervous system spongiform encephalopathies in humans and animals. Prions are distinct from bacteria, viruses and viroids. The predominant hypothesis at present is that no nucleic acid component is necessary for infectivity of prion protein. Further, a prion which infects one species of animal (e.g., a human) will not readily infect another (e.g., a mouse).

A major step in the study of prions and the diseases that they cause was the discovery and purification of a protein designated prion protein ("PrP") [Bolton et al., *Science* 218:1309–11 (1982); Prusiner et al., *Biochemistry* 21:6942–50 (1982); McKinley et al., *Cell* 35:57–62 (1983)]. Complete prion protein-encoding genes have since been cloned, sequenced and expressed in transgenic animals. $PrP^C$ is encoded by a single-copy host gene [Basler et al., *Cell* 46:417–28 (1986)] and is normally found at the outer surface of neurons. A leading hypothesis is that prion diseases result from conversion of $PrP^C$ into a modified form called $PrP^{Sc}$.

It appears that $PrP^{Sc}$ is necessary for both the transmission and pathogenesis of the transmissible neurodegenerative diseases of animals and humans. See Prusiner, S. B., "Molecular biology of prion disease," *Science* 252:1515–1522 (1991). The most common prion diseases of animals are scrapie of sheep and goats, and bovine spongiform encephalopathy (BSE) of cattle [Wilesmith, J. and Wells, *Microbiol. Immunol.* 172:21–38 (1991)]. Four prion diseases of humans have been identified: (1) kuru, (2) Creutzfeldt-Jakob Disease (CJD), (3) Gerstmann-Strassler-Scheinker Disease (GSS), and (4) fatal familial insomnia (FFI) [Gajdusek, D. C., *Science* 197:943–960 (1977); Medori et al., *N. Engl. J. Med.* 326:444–449 (1992)]. The presentation of human prion diseases as sporadic, genetic and infectious illnesses initially posed a conundrum which has been explained by the cellular genetic origin of PrP.

Most CJD cases are sporadic, but about 10–15% are inherited as autosomal dominant disorders that are caused by mutations in the human PrP gene [Hsiao et al., *Neurology* 40:1820–1827 (1990); Goldfarb et al., *Science* 258:806–808 (1992); Kitamoto et al., *Proc. R. Soc. Lond.* 343:391–398. latrogenic CJD has been caused by human growth hormone derived from cadaveric pituitaries as well as dura mater grafts [Brown et al., *Lancet* 340:24–27 (1992)]. Kuru, which for many decades devastated the Fore and neighboring tribes of the New Guinea highlands, is believed to have been spread by infection during ritualistic cannibalism [Alpers, M. P., *Slow Transmissible Diseases of the Nervous System*, Vol. 1, S. B. Prusiner and W. J. Hadlow, eds. (New York: Academic Press), pp. 66–90 (1979)].

The initial transmission of CJD to experimental primates has a rich history beginning with William Hadlow's recognition of the similarity between kuru and scrapie. In 1959, Hadlow suggested that extracts prepared from patients who died of kuru be inoculated into nonhuman primates and that the animals be observed for disease that was predicted to occur after a prolonged incubation period [Hadlow, W. J., *Lancet* 2:289–290 (1959)]. Seven years later, Gajdusek, Gibbs and Alpers demonstrated the transmissibility of kuru to chimpanzees after incubation periods ranging form 18 to 21 months [Gajdusek et al., *Nature* 209:794–796 (1966)]. The similarity of the neuropathology of kuru with that of CJD [Klatzo et al., *Lab Invest.* 8:799–847 (1959)] prompted similar experiments with chimpanzees and transmissions of disease were reported in 1968 [Gibbs, Jr. et al., *Science* 161:388–389 (1968)]. Over the last 25 years, about 300 cases of CJD, kuru and GSS have been transmitted to a variety of apes and monkeys.

The expense, scarcity and often perceived inhumanity of such animal experiments have restricted this work and thus limited the accumulation of knowledge. While the most reliable transmission data has been said to emanate from studies using nonhuman primates, some cases of human prion disease have been transmitted to rodents but apparently with less regularity [Gibbs, Jr. et al., *Slow Transmissible Diseases of the Nervous System*, Vol. 2, S. B. Prusiner and W. J. Hadlow, eds. (New York: Academic Press), pp. 87–110 (1979); Tateishi et al., *Prion Diseases of Humans and Animals*, Prusiner et al., eds. (London: Ellis Horwood), pp. 129–134 (1992)].

The importance of understanding the conversion of $PrP^C$ into $PrP^{Sc}$ has been heightened by the possibility that bovine prions have been transmitted to humans who developed variant Creutzfeldt-Jakob disease (vCJD), G. Chazot, et al., *Lancet* 347:1181 (1996); R. G. Will, et al., *Lancet* 347:921–925 (1996). Earlier studies had shown that the N-terminus of $PrP^{Sc}$ could be truncated without loss of scrapie infectivity, S. B. Prusiner, et al., *Biochemistry* 21:6942–6950 (1982); S. B. Prusiner, et al., *Cell* 38:127–134 (1984) and correspondingly, the truncation of the N-terminus of $PrP^{Sc}$ still allowed its conversion into $PrP^{Sc}$ (M. Rogers, et al., *Proc. Natl. Acad. Sci. USA* 90:3182–3186 (1993)).

Recent studies have advanced our ability to visualize the structural transition of $PrP^c$ to $PrP^{Sc}$ at a molecular level. For example, the N-terminal portion of $PrP^C$ is relatively unstructured and flexible, but assists in stabilizing structural elements within the C-terminal portion. D. G. Donne et al., *Proc. Natl. Acad. Sci. USA* 94:13452–13457 (1997). Furthermore, immunological studies have demonstrated that N-terminal epitopes are cryptic in $PrP^{Sc}$, supporting the idea that this region undergoes profound conformational change during prion propagation. Peretz et al., *J. Mol. Biol.* 273:614–622 (1997).

Despite these advances, our understanding of the structural biology of the pathogenic conversion process remains incomplete in many ways. For example, it is unknown exactly which structural regions of $PrP^C$ are necessary or sufficient for conformational change to occur. It is also unknown which regions of $PrP^{Sc}$ are necessary or sufficient for infectivity. Evidence indicates that prion strain phenomena and species barriers are a result of different PrP conformations, but the precise structural determinants of these conformations have not yet been precisely identified. Telling et al. *Science* 274:2079–2082 (1996); Billeter, et al., *Proc. Natl. Acad. Sci. USA* 94:7281–7285 (1997).

Recent studies have identified four residues of mouse PrP (MoPrP) that appear to interact with protein X, a putative factor postulated to facilitate the conformational change from $PrP^C$ to $PrP^{Sc}$. Telling, et. al. *Cell* 83:79–90 (1995). All four amino acids come together to form the putative protein X binding site in the tertiary structure of recombinant PrP 90–231 and PrP 29–231. D. G. Donne et al., *Proc. Natl. Acad. Sci. USA* 94:13452–13457 (1997); T. L. James et al., *Proc. Natl. Acad. Sci. USA* 94:10086–10091 (1997). However, despite several reports of proteins which bind $PrP^C$, the identity of protein X remains elusive. Finally, although the structures of refolded, recombinant PrP molecules may resemble $PrP^C$, a structural solution for $PrP^{Sc}$ remains lacking.

One method of studying prion disease and the physiological changes inherent in the disease is to alter the physical structure of the $PrP^C$ protein expressed in infected cells to examine the effect on progression of prion-mediated disorders. In particular, the glycosylation sites of $PrP^C$ were initially examined to determine their role in conversion of $PrP^C$ to $PrP^{Sc}$. $PrP^C$ mutants with Thr to Ala substitutions in two NXT consensus glycosylation sites (182 and 198) exhibited increased sporadic conversion to a proteinase K-resistant form following transfection of the mutant constructs in cells, suggesting that the molecule possessed decreased conformational stability and was therefore more likely to undergo the conversion to $PrP^{Sc}$ Taraboulos et al., *PNAS*, 87:8262–8266 (1990). The $PrP^C$ molecule also exhibited aberrant intracellular localization, however, and it was hypothesized that the conversion to $PrP^{Sc}$ could also be due to the location of the precursor mutant $PrP^C$ molecule. The latter hypothesis was strengthened by the expression of a $PrP^C$ with a T183A glycosylation mutation in transgenic mice, which resulted in an altered distribution of $PrP^C$ and an incubation period of >500 following infection with mouse prions. DeArmond et al., *Neuron*, 19:1337–1348 (1997). The aberrant trafficking of this mutant form of $PrP^C$ resulted in accumulation of the $PrP^C$ in the cell body, and a complete absence of $PrP^C$ in the dendritic trees. Since $PrP^{Sc}$ formation is thought to occur on the cell surface, the aberrant trafficking presumably prevented $PrP^{Sc}$ formation and accumulation in these transgenic animals, resulting in the increased incubation period.

Given the time and cost limitations of presently available systems, there is a need in the art for a method of studying the pathogenic conversion process of prion disease in more efficient, time-effective systems. There is thus a need in the art for systems to study prion disease using a time-efficient model for prion infection and progression of prion-mediated disorders.

SUMMARY OF THE INVENTION

The present invention provides a novel PrP protein, and nucleic acids encoding this protein, where the PrP protein is characterized in vivo by 1) incomplete glycosylation relative to glycosylation of wild-type $PrP^C$ and 2) sufficient proper cellular localization, i.e. an ability to be transported to the cell surface in an amount sufficient to allow infectivity. This novel, under-glycosylated PrP, unlike its normal cellular counterpart, can be converted into a protease-resistant isoform by incubation with infectious prions. The invention further provides systems, in vitro, cellular and animal, for the study of prion disorders and methods of using these systems, e.g. the study of the mechanical processes in progression of prion-mediated disease or the identification of new therapeutic agents for treatment of prion-mediated disorders. In such systems, protease-resistant under-glycosylated PrP is generated de novo and can be detected by standard immunoblot techniques.

In one embodiment, the under-glycosylated PrP of the invention is expressed in cell culture. The conversion of under-glycosylated PrP expressed in cell culture can be achieved by inoculating dishes of cells with brain homogenates of prion-diseased animals in as short as 4 days.

In another embodiment, the under-glycosylated PrP of the invention is expressed in the brains of transgenic mice. In a preferred embodiment, the expression of the under-glycosylated PrP is controlled by an inducible promoter.

The present invention also provides non-human transgenic animals for the study and diagnosis of prion-mediated pathologies, with the transgenic animal characterized by a genome artificially altered to contain an exogenous PrP gene of the invention. In a preferred embodiment, the genome is also altered to contain an inducer sequence which effects expression of the exogenous PrP gene. These transgenic animals are characterized by their ability to develop symptoms of prion disease within 200 days or less after being inoculated with infectious prion preparations that would normally only infect a genetically diverse animal. The transgenic animal may additionally have an endogenous gene altered by ablation or modified to express a chimeric form of the gene, and may be either homozygous or heterozygous for these alterations. Preferably, the transgenic animal of the invention is a rat, a hamster, or more preferably a mouse. The genetically diverse animal is preferably a human, a cow, a sheep, a horse, a goat, a deer, a pig, a dog, a cat, a turkey or a chicken.

The invention also features a method for detecting prions in a sample by inoculating a transgenic, non-human mammal, preferably a mouse, with material suspected to be contaminated with prions. The animal inoculated contains a genome artificially altered to express a under-glycosylated PrP gene of the invention, and optionally an inducer sequence which effects expression of the exogenous PrP gene. Prion infectivity can be determined by observing the transgenic animal for a symptom of prion disease, such as ataxia. Ataxia may be detected by direct visual observation of the animals or by means of a pressure-sensitive detector positioned under the feet of the mouse, which may distinguish the pattern of a scrapie ill animal relative to the pattern of an unaffected animal. Alternatively, brain homogenates from the infected animal can be produced and examined for the presence and/or levels of $PrP^{Sc}$.

An object of the invention is to provide an ex vivo system for studying the structural events occurring in conversion.

Another object of the invention is to provide an ex vivo method identifying prions in a sample from a subject suspected of suffering from a prion-mediated disorder.

Another object of the invention is to provide a method for identifying cellular factors that mediate PrP activity, interact with PrP and/or facilitate conversion of $PrP^C$ to $PrP^{Sc}$.

Another object is to provide such a transgenic animal which is used as a disease model and/or to assay for the presence of a material which causes disease.

A feature of the invention is that transgenic cell lines, brain homogenates and/or animals can be infected with a sample irrespective of strain of the infectious prion.

An advantage of the present invention is that infectivity of prions in a sample can be determined rapidly.

These and other objects, advantages, and features of the invention will become apparent to those persons skilled in the art upon reading the details of the chimeric gene, assay method, and transgenic mouse as more fully described below.

DETAILED DESCRIPTION OF PREFERRED EMBODIMENTS

Before the present systems, assays and methods are described, it is to be understood that this invention is not limited to particular methodologies described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the fling date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "$Prnp^{0/0}$ or Prnp-Abl" refers to a transgenic animal which has its PrP gene ablated with the "$^{0/0}$" indicating that both alleles are ablated whereas o/+ indicates only one is ablated. Specifically, the animal being referred to is generally a transgenic mouse which has its PrP gene ablated i.e., a PrP knockout mouse. In that the PrP gene is disrupted no mouse PrP protein is expressed.

The term "sporadic CJD" abbreviated as "sCJD" refers to the most common manifestation of Creutzfeldt-Jakob Disease (CJD). This disease occurs spontaneously in individuals with a mean age of approximately 60 at a rate of 1 per million individuals across the earth.

The term "latrogenic CJD" abbreviated as "iCJD" refers to disease resulting from accidental infection of people with human prions. The most noted example of such is the accidental infection of children with human prions from contaminated preparations of human growth hormone.

The term "Familial CJD" refers to a form of CJD which occurs rarely in families and is inevitably caused by mutations of the human PrP gene. The disease results from an autosomal dominant disorder. Family members who inherit the mutations generally succumb to CJD.

The term "Gerstmann-Strassler-Scheinker Disease" abbreviated as "GSS" refers to a form of inherited human prion disease. The disease occurs from an autosomal dominant disorder. Family members who inherit the underglycosylated gene generally succumb to GSS.

The term "prion" shall mean an infectious particle known to cause diseases (spongiform encephalopathies) in animals including cows and humans. The term "prion" is a contraction of the words "protein" and "infection" and the particles are comprised largely if not exclusively of $PrP^{Sc}$ molecules encoded by a PrP gene. Prions are distinct from bacteria, viruses and viroids. Known prions include those which infect animals to cause scrapie, a transmissible, degenerative disease of the nervous system of sheep and goats as well as bovine spongiform encephalopathies (BSE) or "mad cow" disease and feline spongiform encephalopathies of cats. Four prion diseases known to affect humans are (1) kuru, (2) Creutzfeldt-Jakob Disease (CJD), (3) Gerstmann-Strassler-Scheinker Disease (GSS), and (4) fatal familial insomnia (FFI). As used herein prion includes all forms of prions causing all or any of these diseases or others in any animals used—and in particular in humans, cows and other domesticated farm animals.

The term "PrP gene" is used herein to describe genetic material which expresses proteins (for example those shown in FIGS. 3–5 of U.S. Pat. No. 5,565,186 issued Oct. 15, 1996) and polymorphisms and mutations such as those listed herein under the subheading "Pathogenic Mutations and Polymorphisms". The PrP gene can be from any animal including the "host" and "test" animals described herein and any and all polymorphisms and mutations thereof, it being recognized that the terms include other such PrP genes that are yet to be discovered.

The term "PrP gene" refers generally to any gene of any species which encodes any form of a PrP amino acid sequences including any prior protein, the non-disease form of the protein being referred to as $PrP^{C}$ and the disease form referred to as $PrP^{Sc}$. Some commonly known PrP sequences are described in Gabriel et al., *Proc. Natl. Acad. Sci. USA* 89:9097–9101 (1992) and U.S. Pat. No. 5,565,186 both of which are incorporated herein by reference to disclose and describe such sequences.

The terms "prion preparation", "preparation" and the like are used interchangeably herein to describe a composition suspected of containing prions obtained from brain tissue of mammals. The mammals from which standardized prion preparations are obtained exhibit clinical signs of CNS dysfunction as a result of inoculation with prions and/or due to developing the disease due to their genetically modified make up, e.g., high copy number of PrP genes.

The term "artificial PrP gene" is used herein to encompass the term "chimeric PrP gene" as well as other recombinantly constructed genes which when included in the genome of a host animal (e.g., a mouse) will render the mammal susceptible to infection from prions which naturally only infect a genetically diverse test mammal, e.g., human, bovine or ovine. In general, an artificial gene will include the codon sequence of the PrP gene of the mammal being genetically altered with one or more (but not all, and generally less than 40) codons of the natural sequence being replaced with a different codon—preferably a corresponding codon of a genetically diverse mammal (such as a human). The genetically altered mammal being used to assay samples for prions which only infect the genetically diverse mammal. Examples of artificial genes are mouse PrP genes encoding the sequence as shown in FIGS. 3, 4 and 5 of U.S. Pat. No. 5,565,186, with one or more different replacement codons selected from the codons shown in these Figures for humans, cows and sheep replacing mouse codons at the same position, with the proviso that not all the mouse codons are replaced with differing human, cow or sheep codons. Artificial PrP genes of the invention have mutations that affect glycosylation of the PrP molecule, and: codons of genetically diverse animals; codons and/or codon sequences associated with genetic prion diseases such as CJD; and codons and sequences not associated with any native PrP gene but which, when inserted into an animal, render the animal susceptible to infection with prions which would normally only infect a genetically diverse animal. The introduction of artificial PrP genes may be stable or transient, particularly for cell transfection assays. For example, the artificial PrP gene may be introduced using a viral vector. In this manner, the PrP gene may be introduced to particular tissues or cell types, e.g. CNS tissue.

The terms "chimeric gene," "chimeric PrP gene", and the like are used interchangeably herein to mean an artificially constructed gene containing the codons of a host animal such as a mouse with one or more of the codons being replaced with corresponding codons from a genetically diverse test animal such as a human, cow or sheep. The chimeric PrP genes of the invention all additionally contain mutations that decrease the levels of glycosylation of PrP in vivo. In one specific example the chimeric gene is comprised of the starting and terminating sequence (i.e., —and C-terminal codons) of a PrP gene of a mammal of a host species (e.g. a mouse) and also containing a nucleotide sequence of a corresponding portion of a PrP gene of a test mammal of a second species (e.g. a human). A chimeric gene will, when inserted into the genome of a mammal of the host species, render the mammal susceptible to infection with prions which normally infect only mammals of the second species. The preferred chimeric gene disclosed herein is MHu2M which contains the starting and terminating sequence of a mouse PrP gene and a non-terminal sequence region which is replaced with a corresponding human sequence which differs from a mouse PrP gene in a manner such that the protein expressed thereby differs at nine residues.

The term "genetic material related to prions" is intended to cover any genetic material which affects the ability of an animal to become infected with prions. Thus, the term encompasses any "PrP gene", "artificial PrP gene", "chimeric PrP gene" or "ablated PrP gene" which terms are defined herein as well as mutations and modifications of such which effect the ability of an animal to become infected with prions.

The terms "host animal" and "host mammal" are used to describe animals which will have their genome genetically and artificially manipulated so as to include genetic material which is not naturally present within the animal. For example, host animals include mice, hamsters and rats which have their endogenous PrP gene altered by the insertion of an artificial gene of the present invention.

The terms "test animal" and "test mammal" are used to describe the animal which is genetically diverse from the host animal in terms of differences between the PrP gene of the host animal and the PrP gene of the test animal. The test animal may be any animal for which one wishes to run an assay test to determine whether a given sample contains prions with which the test animal would generally be susceptible to infection. For example, the test animal may be a human, cow, sheep, pig, goat, deer, horse, cat, dog, turkey or chicken, and one may wish to determine whether a particular sample includes prions which would normally only infect the test animal. This is done by including PrP gene sequences of the test animal into the host animal and inoculating the host animal with prions which would normally only infect the test animal.

The terms "genetically diverse animal" and "genetically diverse mammal" are used to describe an animal which includes a native PrP codon sequence of the host animal which differs from the genetically diverse test animal by 17 or more codons, preferably 20 or more codons, and most preferably 28–40 codons. Thus, a mouse PrP gene is genetically diverse with respect to the PrP gene of a human, cow or sheep, but is not genetically diverse with respect to the PrP gene of a hamster.

The terms "ablated PrP gene", "disrupted PrP gene", and the like are used interchangeably herein to mean an endogenous PrP gene which has been altered (e.g., add and/or remove nucleotides) in a manner so as to render the gene inoperative. Examples of non-functional PrP genes and methods of making such are disclosed in Büeler, H., et al "Normal development of mice lacking the neuronal cell-surface PrP protein" *Nature* 356:577–582 (1992) which is incorporated herein by reference. Both alleles of the genes are preferably disrupted.

The terms "hybrid animal", "transgenic hybrid animal" and the like are used interchangeably herein to mean an animal obtained from the cross-breeding of a first animal having an ablated endogenous PrP gene with a second animal which includes a chimeric gene or artificial PrP gene of the invention. For example a hybrid mouse is obtained by cross-breeding a mouse with an ablated mouse PrP gene with a mouse containing under-glycosylated chimeric PrP genes. The term hybrid includes any offspring of a hybrid including inbred offspring of two hybrids provided the resulting offspring is susceptible to infection with prions with normal infect only a genetically diverse species and the symptoms of the infection are observable in about 350 days or less, preferably 250 or less.

The terms "susceptible to infection", "susceptible to infection by prions", and the like are used interchangeably herein to describe a transgenic or hybrid test animal of the invention which develops a prion disease if inoculated with prions which would normally only infect a genetically diverse test animal. The terms are used to describe a transgenic or hybrid animal of the invention such as a transgenic mouse Tg(MHu2M) which, without the chimeric PrP gene, would not be susceptible to infection with a human prion (less than 20% chance of infection) but with the chimeric gene is susceptible to infection with human prions (80% to 100% chance of infection). If an animal is susceptible to infection with a particular prion that animal, if inoculated with the prion, will show symptoms of prion disease infection in about 350 days or less, preferably 250 days or less.

The term "incubation time" shall mean the time from inoculation of an animal with a prion until the time when the animal first develops detectable symptoms of disease resulting from the infection. A reduced incubation time is one year or less, preferably about 200 days±50 days or less, more preferably about 50 days±20 days or less.

Abbreviations used herein include:

CNS for central nervous system;

BSE for bovine spongiform encephalopathy;

CJD for Creutzfeldt-Jakob Disease;

FFI for fatal familial insomnia;

GSS for Gerstmann-Strassler-Scheinker Disease;

Hu for human;

HuPrP for a human PrP;

Mo for mouse;

Bo for bovine;

MoPrP for a mouse PrP;

SHa for a Syrian hamster;

SHaPrP for a Syrian hamster PrP;

Tg for transgenic;

Tg(SHaPrP) for a transgenic mouse containing the PrP gene of a Syrian hamster;

Tg(HuPrP) for transgenic mice containing the complete human PrP gene;

Tg(ShePrP) for transgenic mice containing the complete sheep PrP gene;

Tg(BoPrP) for transgenic mice containing the complete cow PrP gene;

$PrP^{Sc}$ for the scrapie isoform of the PrP;

$MoPrP^{Sc}$ for the scrapie isoform of the mouse PrP;

MHu2M for a chimeric mouse/human PrP gene wherein a region of the mouse PrP gene is replaced by a corresponding human sequence which differs from mouse PrP at 9 codons;

MBo2M for a chimeric mouse/bovine PrP gene wherein a region of the mouse PrP gene is replaced by a corresponding bovine sequence which differs from mouse PrP at 8 codons.

Tg(MHu2M) mice are transgenic mice of the invention which include the chimeric MHu2M gene;

$MHu2MPrP^{Sc}$ for the scrapie isoform of the chimeric human/mouse PrP gene;

$PrP^{CJD}$ for the CJD isoform of a PrP gene;

$Prnp^{0/0}$ for ablation of both alleles of an endogenous PrP gene, e.g., the MoPrP gene;

Tg(BoPrP)/$Prnp^{0/0}$ for a transgenic mouse obtained with a bovine PrP gene (BoPrP);

Tg(MHu2M)/$Prnp^{0/0}$ for a mouse with a chimeric (mouse/human) PrP gene (WHu2M) with both alleles of the endogenous mouse PrP gene disrupted;

Tg(MBo2M)$Prnp^{0/0}$ for a transgenic mouse with a chimeric (mouse/bovine) PrP gene (MBo2M) with both alleles of the endogenous mouse PrP gene disrupted;

FVB for a standard inbred strain of mice often used in the production of transgenic mice since eggs of FVB mice are relatively large and tolerate microinjection of exogenous DNA relatively well.

GENERAL ASPECTS OF THE INVENTION

The present invention is based on the discovery that expression of an under-glycosylated $PrP^C$ protein in cells renders these cells susceptible to infection by prions, when the cells are exposed to preparations containing prions, allowing these cells to produce de novo $PrP^{Sc}$. Although previous Thr to Ala substitutions in the glycosylation sites of PrP resulted in conformational instability, the resulting $PrP^C$ molecules displayed an aberrant cellular localization and resulted in a very long prion incubation period when expressed in transgenic mice. Surprisingly, mutations of the present invention, e.g. Asn to Gin mutations in the PrP glycosylation site, result in a $PrP^C$ molecule that are conformationally unstable but properly localized at the cell surface in amounts that allow conversion of $PrP^C$ to $PrP^{Sc}$ upon infection. The conversion of the under-glycosylated $PrP^C$ is rapid, allowing for quick detection of prions in the cells expressing this variant PrP and allowing inoculation transgenic mice to show signs of infection in 250 days or less.

Currently, the most sensitive bioassay for prion infection, the intracerebral inoculation, lasts several months even if transgenic mice overexpressing PrP are used as recipient animals for intracerebral infection. Diagnosis of transmissibility is made only upon appearance of characteristic symptoms like ataxia, and, when examining the brain, typical neuropathological features of diseased brain tissue such as vacuolation, astrogliosis, and nerve cell loss. In vitro methods of diagnosing prion disease in a suspected diseased brain, such as detection of the presence of protease-resistant PrP on Western blots, is limited by the sensitivity of the immunological assay. The present invention provides an ex vivo method of detection, combining the sensitivity and specificity of an animal bioassay and the rapidity of a Western blot procedure.

Cellular systems expressing under-glycosylated $PrP^C$ provide methods of transient or permanent overexpression of an under-glycosylated PrP in a particular cell line, incubation of these cells with the tissue suspension or body fluid of interest, and examination of the de novo formation of prions with a conventional method like Western blotting allows detection of prions in a sample without the limitations found in currently available bioassays. The rapid replication of prions in this cell line overexpressing under-glycosylated PrP is used to amplify minute amounts of prions present in various tissues.

In one embodiment, the PrP encodes a double mutation where the two asparagines in the glycosylation sites are substituted with another amino acid. In a preferred embodiment, the two asparagines are substituted to glutamine (N180Q/N196Q). The under-glycosylated PrP overcomes the problems of cell trafficking while still preventing glycosylation. Correct transportation of this under-glycosylated PrP into the same compartments as its wild-type counterpart has been experimentally shown by immunofluorescence and co-transfection studies.

This rapid bioassay is a major improvement in diagnosing prion diseases, since available bioassays in cell lines were limited to particular strains of prions and took at least 4 weeks to convert cell-resident PrP. Alternatively, inoculation of available transgenic mice takes 2 to 9 months, depending on the species of prion used (Fischer et al., 1996; Prusiner, 1997; Telling et al., 1994). The present invention of an under-glycosylated PrP overcomes these limits of prior art in that cell lines can be infected with brain homogenates of prion-diseased animals irrespective of strains with an unsurpassed rapidity.

PrP NUCLEIC ACID COMPOSITIONS

The term “under-glycosylated PrP” as used within the present specification generically designates PrP genes encoding proteins altered with respect to their ability to be glycosylated relative to the normal cellular form of PrP. The term encompasses PrP from any species, e.g. homologs from rat, bovine, human, mouse, guinea pig, etc., and their alternate forms. Used generically, this term encompasses different isoforms, polymorphisms, mutations and variant sequences, so long as the under-glycosylated protein's cellular distribution is not affected. The term is also intended to mean the open reading frame encoding specific under-glycosylated polypeptides, introns, and adjacent 5' and 3' non-coding nucleotide sequences involved in the regulation of expression, up to about 1 kb beyond the coding region, but possibly further in either direction. The DNA sequences encoding PrP may be cDNA or genomic DNA or a fragment thereof. The gene may be introduced into an appropriate vector for extrachromosomal maintenance or for integration into the host.

A genomic sequence of interest in the present invention comprises the altered nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kb or smaller; and substantially free of flanking chromosomal sequence.

The under-glycosylated PrP sequence, including flanking promoter regions and coding regions, may be additionally under-glycosylated in various ways known in the art to generate targeted changes in promoter strength, sequence of the encoded protein, etc. The sequence changes may be substitutions, insertions or deletions. Deletions may include large changes, such as deletions of a domain or exon. Other modifications of interest include epitope tagging, e.g. with the FLAG system, HA, etc. For studies of subcellular localization, fusion proteins with green fluorescent proteins (GFP) may be used. Such under-glycosylated genes may be used to study structure-function relationships of prion polypeptides, or to alter properties of the proteins that affect their function or regulation.

Techniques for in vitro mutagenesis of cloned genes are known. Examples of protocols for scanning mutations may be found in Gustin et al., *Biotechniques* 14:22 (1993); Barany, *Gene* 37:111–23 (1985); Colicelli et al., *Mol Gen Genet* 199:537–9 (1985); and Prentki et al., *Gene* 29:303–13 (1984). Methods for site specific mutagenesis can be found in Sambrook et al., *Molecular Cloning: A Laboratory Manual*, CSH Press, pp. 15.3–15.108 (1989); Weiner et al., *Gene* 126:3541 (1993); Sayers et al., *Biotechniques* 13:592–6 (1992); Jones and Winistorfer, *Biotechniques* 12:528–30 (1992); Barton et al., *Nucleic Acids Res* 18:7349–55 (1990); Marotti and Tomich, *Gene Anal Tech* 6:67–70 (1989); and Zhu, *Anal Biochem* 177:120–4 (1989).

The mutations present in the PrP of the invention may be introduced into any genetic background, and the PrP gene itself may have any number of polymorphisms or specific mutations associated with disease states. There are a number of mutations and polymorphisms existing with respect to the PrP gene of different species. A number of the mutations and polymorphisms are listed in the “Mutation Table” provided below. It is believed that additional mutations and polymorphisms exist in all species within the PrP gene. Animals with a PrP gene which is heterozygous at a particular point could be bred with other animals which are heterozygous at that point in order to produce offspring which include those with a homozygous PrP gene of the type desired. Substitutions in the PrP transgene may be made with an amino acid which is biochemically quite different from the amino acid at that position which is known to render the animal susceptible to prion infection. Thus, if a basic and/or polar amino acid is present at the critical site that site could be replaced with an acidic and/or nonpolar amino acid. With these criteria in mind some trial and error would be required. Acidic amino acids should be substituted with basic amino acids and vice versa. Polar amino acids should be substituted with nonpolar amino acids and vice versa. Such mutations may increase the susceptibility of the transgenic animals for the uses described herein.

There are a number of known pathogenic mutations in the human PrP gene. Further, there are known polymorphisms in the human, sheep and bovine PrP genes. The following is a list of such mutations and polymorphisms:

MUTATION TABLE

| Pathogenic human mutations | Human Polymorphisms | Sheep Polymorphisms | Bovine Polymorphisms |
|---|---|---|---|
| 2 octarepeat insert | Codon 129 Met/Val | Codon 171 Arg/Gln | |
| 4 octarepeat insert | Codon 219 Glu/Lys | Codon 136 Ala/Val | |
| 5 octarepeat insert | | Codon 154 Arg/His | 5 octarepeat insert |
| 6 octarepeat insert | | | 6 octarepeat insert |
| 7 octarepeat insert | | | 7 octarepeat insert |
| 8 octarepeat insert | | | |
| 9 octarepeat insert | | | |
| Codon 102 Pro-Leu | | | |
| Codon 105 Pro-Leu | | | |
| Codon 117 Ala-Val | | | |
| Codon 145 Stop | | | |
| Codon 178 Asp-Asn | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |
| Codon 232 Met-Ala | | | |

In order to provide further meaning to the above chart demonstrating the mutations and polymorphisms, one can refer to the published sequences of PrP genes. For example, a chicken, bovine, sheep, rat and mouse PrP gene are disclosed and published within Gabriel et al., *Proc. Natl. Acad. Sci. USA* 89:9097–9101 (1992). The sequence for the Syrian hamster is published in Basler et al., *Cell* 46:417–428 (1986). The PrP gene of sheep is published by Goldmann et al., *Proc. Natl. Acad. Sci. USA* 87:2476–2480 (1990). The PrP gene sequence for bovine is published in Goldmann et al., *J. Gen. Virol.* 72:201–204 (1991). The sequence for chicken PrP gene is published in Harris et al., *Proc. Natl. Acad. Sci. USA* 88:7664–7668 (1991). The PrP gene sequence for mink is published in Kretzschmar et al., *J. Gen. Virol.* 73:2757–2761 (1992). The human PrP gene sequence is published in Kretzschmar et al., *DNA* 5:315–324 (1986). The PrP gene sequence for mouse is published in Locht et al., *Proc. Natl. Acad. Sci. USA* 83:6372–6376 (1986). The PrP gene sequence for sheep is published in Westaway et al., *Genes Dev.* 8:959–969 (1994). These publications are all incorporated herein by reference to disclose and describe the PrP gene and PrP amino acid sequences.

The under-glycosylated PrP nucleic acids of the invention may also encode a known epitope, such as a polyhistidine or c-myc epitope tag, which is inserted into an expressed region of the sequence. The epitope is inserted such that it is in-frame and thus properly translated. The epitope sequences may be added in-frame to various sites of the full-length protein. Preferably, the exogenous epitope is inserted in-frame carboxy to the end of the translated PrP polypeptide.

The epitope tag sequences may alter solubility of the encoded PrP as well, and this ability may be position dependent. Thus varying the site may alter the solubility, conformation, and activity of the full-length protein.

Any epitope tag currently known in the art may be used, although preferably the epitope used is comprised of charged residues, and more preferably is a polyhistidine tag. The epitope tag is preferably comprised of polar weakly basic residues such as arginine, or lysine and more preferably histidine. Polar residues of any type would be useful in increasing solubility.

CELLULAR SYSTEMS OF THE INVENTION

The present invention provides a cellular system for the study and diagnosis of prion-mediated diseases, and methods of using such cellular systems. The cellular systems allow for the study of mechanisms involved in prion infection and disease without having to use an animal model. Cellular systems of the invention offer an advantage in that they are less costly than animal systems, offer faster results than animal systems, and are more humane since they do not require the sacrifice of animals to study the cellular mechanisms of the disease progression.

Knowledge of the conditions under which scrapie infectivity is generated de novo is useful in the development of assays to identify compounds able to inhibit the generation of $PrP^{Sc}$. Compounds able to inhibit the ex vivo conversion of $PrP^{C}$ to $PrP^{Sc}$ could be useful for the treatment and prevention of prion-mediated diseases in animal and human subjects at risk. Such cellular systems provide numerous methods for investigation, including: an ex vivo mechanism to study the physiological basis and progression of the disease, e.g. molecular interactions involved in prion infection and the progression of prion-mediated disease; methods for identifying cellular factors that interact with $PrP^{C}$ and/or $PrP^{Sc}$; diagnosis of samples from animals that are potentially infected with prions without having to sacrifice an animal in the process; and assays to examine the efficacy and toxicity of potential therapeutic agents that block prion infection and/or the progression of a prion-mediated disorder. These and other uses for the cellular model of prion infection will be obvious to one skilled in the art upon reading this disclosure.

The PrP of the invention may be expressed in any cell type, including prokaryotic cells, such as *E. coli*, and eukaryotic cells, including cells from *S. cerevisae, D. melanogaster, X laevis*, avian cells, mammalian expression systems, and the like. Expression of the PrP of the invention finds particular use with mammalian cells, such as CHO and COS cells, since these cells have mammalian cellular components and are particularly useful for the study and diagnosis of prion-mediated disorders. Preferably, the cells for use in a cellular system of the invention are neuronal mammalian cells, and more preferably N2a cells. The cells may be transiently transfected or, more preferably, stably transfected and maintained in long-term culture. Exemplary methods for transfection of cells with PrP nucleic acids can be found in Sambrook et al., *Molecular Cloning: A Laboratory Manual* (3rd ed.) which is incorporation by reference herein to aid one skilled in the art in these techniques.

In one embodiment of the invention, a sample may be assayed for the presence of infectious prions by exposing a sample to be tested to a cellular system expressing the under-glycosylated form of PrP, allowing for sufficient incubation time, and then assaying the culture for the presence of prions.

In another embodiment, the PrP of the invention is transfected directly into the cells of the sample to be assayed, and the level of prions in these cells determined after an appropriate incubation period. The ability of the PrP of the invention to readily transform into the infectious form of PrP allows primary cultures to be manipulated and assayed directly following transfection of under-glycosylated PrP into such cells.

DETECTION OF PRION PROTEIN IN A SAMPLE

Once a sample is tested in the ex vivo system of the invention, sample may be assayed by a variety of known techniques. The examples and comparative examples put forth herein utilize a conformation-dependent immunoassay (CDI) of the type which is disclosed and described within PCT Publication WO 98/37411 published Feb. 20, 1998. However, other types of protein detection assays could be utilized. For example, the sample can be assayed using antibodies of the type disclosed and described within U.S. Pat. No. 5,846,533 issued Dec. 8, 1998, which is incorporated herein by reference in its entirety in order to disclose and describe specific types of assays which might be used on the samples prepared in accordance with the present invention.

The method requires beginning with a sample which is divided into two portions. The first portion of the sample is contacted with a binding partner. The binding partner has a higher affinity for the first conformation of the protein than it has for the second pathogenic conformation of the protein. The binding partner is typically an antibody such as labeled 3F4. After allowing the binding partner to bind to a protein in the first conformation the concentration of the binding partner/protein complexes formed is determined.

A second portion of the sample is then treated in a manner which causes the binding affinity of the protein in the second conformation to be enhanced with respect to the binding partner. This treatment can include a variety of different methodologies and often involves exposure of the sample to a protease for a sufficient period of time under sufficient conditions so as to cause the protein in the second pathogenic conformation to become more relaxed and therefor more likely to bind to the binding partner.

The treated second portion is then brought into contact with the binding partner. After binding between the proteins and binding partners are allowed to occur the concentration of binding partner/protein complexes formed in this second treated portion is determined.

If the sample contained no protein in the second, pathogenic conformation of the protein then the treatment will have little effect. However, the treatment will have some effect on the first conformation of the protein and is likely to increase it's binding affinity to the binding partner in some small degree. Accordingly, an adjustment must be made in the second concentration in order to provide an adjusted concentration which adjustment compensates for the increased affinity of the protein of the first conformation for the binding partner resulting from the treatment.

After obtaining the first concentration and the adjusted concentration the two are compared to each other. If the adjusted concentration is greater than the first concentration such is an indication of the presence of protein in the second pathogenic conformation in the original sample.

It is possible to carry out variations on the confirmation-dependent immunoassay. One variation which is described in detail in published PCT application WO 98/37411 does not require that the original sample be broken into first and second portions. The treatment process is carried out on a sample and the concentration is determined. That concentration is then compared with a known standard (previously obtained on a statistically significant group of samples) in order to determine if the sample being tested contains prions.

However, it is pointed out that the present invention is not limited to the use of such protein assay methodology. Other assays could be used and other assays will, no doubt, be developed which could utilize the samples prepared in accordance with the present invention in order to obtain accurate results.

IDENTIFICATION OF COMPOUNDS THAT INTERACT WITH $PrP^C$ OR $PrP^{Sc}$

In one aspect, the present invention provides novel assays useful in identifying inhibitors of the formation of a $PrP^{Sc}$-like complex resulting from PrP peptide binding to $PrP^C$. Although ex vivo assays of the present invention can be configured in a number of ways, in a preferred configuration, a test compound is contacted with cells expressing the under-glycosylated $PrP^C$. The cell can be examined for prion protein complex in any number of ways, including immunoprecipitation. Percent sedimentation, protease resistance, and conformation are determined by methods known in the art, such as those methods described below. Formation of a $PrP^{Sc}$-like complex in the presence of a test compound is compared to complex formation in the absence of the test compound (control).

A compound identified by the assay method of the invention as inhibiting complex formation can be tested in an animal model of a $PrP^{Sc}$-mediated disease, and its ability to inhibit $PrP^{Sc}$ induction in vivo or treat a $PrP^{Sc}$-mediated disease determined. As defined above, treatment of a $PrP^{Sc}$-mediated disease includes obtaining a therapeutically detectable and beneficial effect on a patient suffering from a $PrP^{Sc}$-mediated disease.

The documented competition of the anti-PrP monoclonal antibody 3F4 for the interaction between $PrP^C$ and $PrP^{Sc}$ provides an alternate strategy for an assay to screen for compounds able to block prion induction. In one embodiment, $PrP^C$ is derivatized, e.g., with Streptavidin, and immobilized to a solid support, for example, the bottom of the wells of a 96-well plate. Candidate compounds are tested for the ability to displace 3F4 from $PrP^C$. Binding is quantitated through standard measures, for example, by determining the amount of free antibody. Variations in this assay include use of various $PrP^C$-like molecules from recombinant sources.

IN VITRO DRUG EFFICACY EVALUATION

The cellular systems of the invention can be used in determined potential efficacy of a therapeutic agent directed at prion-mediated disorders. Compounds can be contacted with cells expressing the under-glycosylated PrP of the invention, and the effect of this compound on infectivity, progression of the disease, formation of amyloid plaques, etc., determined. The drug may be determined efficacious if it: (1) increases the rate at which the harmful protein is cleared from the system as compared to the rate it is cleared from the system of the mouse with no drug; (2) prevents initial prion infection; and/or (3) retards or halts the progression of the prion development. Compounds that show promise in an in vitro system can be further studied to determine their efficacy in vivo.

TRANSGENIC ANIMALS

The term "transgene" is used herein to describe genetic material that has been or is about to be artificially inserted into the genome of a cell, particularly a mammalian cell for implantation into a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the germine sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

The exogenous PrP gene is altered to prevent complete glycosylation of the molecule while maintaining proper cellular localization of the produced under-glycosylated PrP potein. The mutations to achieve these characteristics may be in any suitable genetic background. For example, mutations to the glycosylation sites may be in a wild type background, in a background with naturally occurring polymorphisms, or in a background with genetically manipulated sequences, e.g. deletions, substitutions or insertions in the coding or non-coding regions. The introduced under-glycosylated PrP coding sequence is usually operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g. transcriptional activator proteins, are bound to the regulatory sequence(s). In some cases the exogenous transgene sequences are ultimately deleted from the genome, leaving a net change to the native sequence.

In the present invention, transgenic knockouts may additionally have a partial or complete loss of function in one or both alleles of the endogenous PrP gene. Preferably, the target gene expression is undetectable or insignificant. A knock-out of an endogenous PrP gene means that function of the PrP protein has been substantially decreased so that expression is not detectable or only present at insignificant levels. This may be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. Different approaches may be used to achieve the "knock-out." See U.S. Pat. Nos. 5,464,764, 5,627,059 and related patents and publications to Capecchi et al. A chromosomal deletion of all or part of the native gene may be induced, including deletions of the non-coding regions, particularly the promoter region, 3' regulatory sequences, enhancers, or deletions of gene that activate expression of PrP genes. A functional knock-out may also be achieved by the introduction of an anti-sense construct that blocks expression of the native genes (for example, see Li and Cohen, *Cell* 85:319–329 (1996)). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

DNA constructs for homologous recombination will comprise at least a portion of the PrP gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al., *Methods in Enzymology* 185:527–537 (1990).

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. See U.S. Pat. Nos. 5,387,742, 4,736,866 and 5,565,186 for methods of making transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for under-glycosylated cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allergenic or congenic grafts or transplants, or in in vitro culture.

TRANSGENIC ANIMALS WITH INDUCIBLE ENDOGENOUS SEQUENCES

Transgenic animals with an inducible endogenous genes that may be detrimental at some point in development may be manipulated for purposes of the invention by placing the under-glycosylated PrP under an inducible promoter. For example of PrP expression using such systems, see U.S. Ser. No. 09/052,963 which is incorporated herein by reference. Such animals would not express the under-glycosylated PrP gene until it was necessary for purposes of the assay, thus allowing the animals to suppress any potential effects of the transgene when such expression is unnecessary. For example, the expression of the under-glycosylated PrP allele can be suppressed throughout development, and then expression of the PrP gene can be used to advance progression of the disease in mature animals. The establishment of a transgenic line free from potential developmental problems but with the ability to rapidly form prions in response to a contaminated sample would be a major advantage in assays to detect prions in a sample.

The creation of transgenic animals with altered endogenous PrP gene is described in U.S. Pat. No. 5,698,763 to Weissmann. It has been proposed to disrupt the endogenous PrP gene completely in animals to prevent development and progression of prion-mediated disease. The transgene encoding the PrP of the present invention may be introduced into animals with a $PrP^{0/0}$ background, thus leaving the under-glycosylated PrP as the only PrP expressed in the transgenic animal. Although the under-glycosylated PrP gene will allow infection by different strains of prions, and thus a species-specific transgene is not a requirement, the under-glycosylated PrP can be tailored depending on the species that is to be tested. For example in human testing an under-glycosylated human PrP transgene can be used and for bovine testing an under-glycosylated bovine transgene can be used, and in particular specific polymorphisms and/or mutations can be introduced to study particular prion-mediated disorders, e.g. mutations found in human CJD can be altered in the transgene.

The under-glycosylated PrP transgene of the present invention will allow the study of progression of prion-mediated disorders in an animal model which has a much shorter period of incubation for such diseases. Such studies may examine biological phenomena such as the levels of expression needed for physiological symptoms to appear, the reversibility of the morphological symptoms following initial stages of the disease, and the like.

TEST ANIMAL

Although a variety of different test animals could be used for testing for the presence of prions within a sample, preferred host animals are mice and hamsters, with mice being most preferred in that there exists considerable knowledge on the production of transgenic animals. Other possible host animals include those belonging to a genus selected from Mus (e.g. mice), Rattus (e.g. rats), Oryctolagus (e.g. rabbits), and Mesocricetus (e.g. hamsters) and Cavia (e.g., guinea pigs). In general mammals with a normal full grown adult body weight of less than 1 kg which are easy to breed and maintain can be used. The host PrP gene can be changed to include codons from genetically diverse PrP genes from test animals belonging to a genus selected from Bos, Ovis, Sus and Homo. Preferably, a mouse host PrP gene is changed to include codons from a human, cow or sheep PrP gene, with human being most preferred. Humans are preferred because an important object of the invention is to use the animal to test a sample of material to determine if that material has prions which will infect a human and cause a human to develop a CNS disease such as CJD. Preferred transgenic animals are disclosed in U.S. Pat. No. 5,565,186 issued Oct. 15, 1996 and WO 97/04814 published Feb. 13, 1997 which are incorporated herein by reference to disclose transgenic animals and methods of making and using such.

The genetic material which makes up the PrP gene is known for a number of different species of animals (see Gabriel et al., *Proc. Natl. Acad. Sci. USA* 89:9097–9101 (1992)). Further, there is considerable homology between the PrP genes in different mammals. For example, see the amino acid sequence of mouse PrP compared to human, cow and sheep PrP in FIGS. 3, 4 and 5 wherein only the differences are shown. Although there is considerable genetic homology with respect to PrP genes, the differences are significant in some instances. More specifically, due to small differences in the protein encoded by the PrP gene of different mammals, a prion which will infect one mammal (e.g. a human) will not normally infect a different mammal (e.g. a mouse). Due to this "species barrier," it is not generally possible to use normal animals, (i.e., animal which have not had their genetic material related to prions manipulated) such as mice to determine whether a particular sample contains prions which would normally infect a different species of animal such as a human.

ENDOGENOUS PrP STATUS OF TEST ANIMALS

Commercially useful transgenic animals are preferably small and easy to reproduce, thus, host animals such as mice, hamsters, guinea pigs and rats are preferred, with mice being most preferred. In order for the transgenic animals to be useful, it is necessary for the animals to be susceptible to infection with prions which normally infect only genetically diverse test animals, and in particular animals of commercial significance for testing, such as humans, cows, deer, horses, sheep, pigs, cats, dogs and chickens, with humans being most preferred. Further, for the transgenic and hybrid animals to be useful in a practical and commercial sense, it is necessary for the animals to demonstrate symptoms of the disease within a relatively short period after inoculation, and for a very high percentage of the animals to demonstrate symptoms of the disease after inoculation.

When the entire PrP gene of a test animal (such as a human) is made functional in the host animal (such as a mouse) the resulting transgenic animal (with a low copy number of human PrP genes) is not susceptible to infection with human prions. Infection would occur if the endogenous PrP gene of the host animal is ablated. Furthermore, if only some of the codons differing between the host and the test animal are switched, the resulting transgenic animal is susceptible to infection with prions which normally only infect the test animal.

As the copy number of the artificial gene in the transgenic animal is increased, the incubation time in some cases decreases. In addition, certain genetic defects resulting in prion diseases have different genetic defects in their PrP gene, and by matching the defects in any transgenic animal will render that animal more susceptible to infection with prions from the diseased human.

With this knowledge, we deduced that it is possible to produce a transgenic animal wherein all of the PrP gene of the host animal is replaced with the PrP gene of a test animal with an attached inducible sequence, thus obtaining a useful transgenic animal which is susceptible to infection with prions which normally only infect the test animal by substantially increasing the copy number of the test animal's PrP gene in the host animal and preferably also ablating the endogenous PrP gene. The copy number can be substantially increased without affecting the survivability of the developing animal by turning expression off during development.

Based on the above, it can be understood that the preferred status of the endogenous gene of the transgenic animals are (1) animals such as mice which include a chimeric PrP gene, i.e., only a portion, but not all, of their PrP gene replaced with a corresponding portion of the under-glycosylated glycosylation sites or (2) animals with an ablated endogenous PrP gene and a PrP gene from another animal such as a human most preferable where that human PrP gene has a mutation which prevents proper glycosylation of the molecule. These genotypes enhance the ability of the inducible transgenic system to detect prion infectivity of a genetically diverse animal with a shorter incubation period. Details regarding construction and testing of animals with either chimeric PrP genes or ablated endogenous PrP genes can be found in U.S. Ser. No. 08/509,261, which is incorporated herein in its entirety.

IN VIVO DRUG EFFICACY EVALUATION

Transgenic animals of the invention can be used to evaluate the efficacy of drugs. In its simplest form, the exogenous gene is expressed in two mice and the drug is administered to one but not the other mouse. The effect of the drug on inhibiting the progress of disease as compared to the mouse with no drug is then determined. Measurements are taken over time for both mice to determine the rate at which harmful protein is cleared from the system of each mouse. The drug is determined efficacious if it increases the rate at which the harmful protein is cleared from the system as compared to the rate it is cleared from the system of the mouse with no drug.

EVALUATION OF LOCOMOTOR AND MOTOR COORDINATION DEFICITS FOR RAPID DIAGNOSIS OF CEREBELLAR SCRAPIE PROGRESSION

The diagnosis of scrapie in rodents involves the detection of at least two classical neurological signs associated with prion diseases as well as the progression of these signs over time. Classical clinical signs are: agressivity, ataxia, dysmetria, tremor, head-bobbing, lack of righting reflex, convulsions, kyphosis, head tilt, tail rigidity, bradykinesia, proprioceptive deficits, masked facies, loss of deep pain sensation, circling and paralysis. The use of a system of the present invention, whether inducible or not, where PrP expression is predominantly localized within the cerebellum, facilitates the detection of replicating prions as the neurodegeneration can be followed by scoring ataxia or disorders of movement, gait, equilibrium and coordination associated with cerebellar degeneration.

To diagnose animals exhibiting scrapie sickness in a shorter period of time, a pressure-sensitive measurement system may be employed to detect and record an inoculated animal's physiological changes, and specifically its motor skills. One example of such a pressure sensitive system that would be effective in monitoring changes in walking is a platform with a piezoelectric ground reaction force (GRF) measurement system such as that used in the Gaitway Instrumented Treadmill (Kistler Biomechanics, Winterthut, Switzerland). Such a system has the ability to measure vertical ground reaction force and center of pressure for complete, multiple foot strikes. The system also has an integrated software system that can distinguish between left and right strikes and measure vertical force, center of pressure, and temporal gait parameters. A database can keep track of trials by subject name, identification number, or other user-specified classification. Multiple trials can be overlaid on a single graph, and the progression of a single subject examined over time. The time base can be varied to view data in absolute time, relative time, percent contact, percent step, and percent gait cycle.

Using such systems for the early detection of scrapie disease can also be achieved more by the systematic quantitative evaluation of these parameters over time using apparatus designed for such purpose.

Another method of evaluating motor coordination is a rotorod test (Sakaguchi et al.). Animals are placed on a rotating rod, whose rotating frequency is steadily increased from 10 rpm until the animals falls from it. The animal is subjected to ten trials and its best score recorded as its score on that given day. This test would offer a quantitative measurement of motor skills over the progression of prion disease and permit the early detection of motoric deficiencies. Other systems with the ability to distinguish motor skill abilities may also be employed, as will be obvious to those skilled in the art.

STANDARDIZED PRION PREPARATION

For both cellular and animal assays used to study prion progression, infectivity, and/or the mechanistic interactions involved in prion disease, standardized preparations of prions may be used to decrease the variability of the studies. Although the preparation can be obtained from any animal it is preferably obtained from a host animal which has brain material containing prions of a test animal. For example, a Tg mouse containing a human prion protein gene can produce human prions and the brain of such a mouse can be used to create a standardized human prion preparation. The preparation can be further standardized, by repeating the above process. More specifically, per the above process some prion containing material must be used to inoculate the transgenic mice. The source of that prion containing material may itself be unpredictable and result in infecting transgenic mice in different ways. Thus, if the transgenic mice are infected with a nonstandard material some may develop the symptoms of prion disease at different rates and some may not develop symptoms at all. If a group of mice which develops symptoms of prion disease at the same time are sacrificed and their brains extracted and homogenized such will create a relatively standard prion preparation.

In that the preparation is to be a "standard" it is preferably obtained from a battery (e.g., 100; 1,000, or more animals) of substantial identical animals. For example, 100 mice all containing a very high copy number of human PrP genes (all polymorphisms and mutations) would spontaneously develop disease and the brain tissue from each could be combined to make a useful standardized prion preparation. The preparation of such standards, and animals useful in the production of such standards, is disclosed in U.S. Ser. No. 09/199,523, which is incorporated herein by reference.

By using standardized prion preparations it is possible to create extremely dilute compositions containing the prions. For example, a composition containing one part per million or less or even one part per billion or less can be created. Such a composition can be used to test the sensitivity of the transgenic mice of the invention in detecting the presence of prions in the sample.

Prion preparations are desirable in that they will include a constant amount of prions and are extracted from an isogeneic background. Accordingly, contaminates in the preparations will be constant and controllable. Standardized prion preparations will also be useful as controls in the carrying out of bioassays in order to determine the presence, if any, of prions in various pharmaceuticals, whole blood, blood fractions, foods, cosmetics, organs and in particular any material which is derived from an animal (living or dead) such as organs, blood and products thereof derived from living or dead humans. Thus, standardized prion preparations will be valuable in validating purification protocols where preparations are spiked and reductions in titer measured for a particular process.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

Mutations are introduced into human PrP sequences to alter two known glycosylation sites of the molecule. A mouse-hamster chimeric PrP transgene (MHM2) is mutagenized to contain a double mutation where the two glycosylation sites are substituted from asparagine to glutamine (N180Q/N196Q), and cloned into a pSPOX expression vector. The PrP molecule was mutagenized using a mismatched oligonucleotide primer and PCR amplification. Following amplification, the mutated PrP DNA is digested with unique restriction endonucleases to allow directional cloning into the pSPOX vector. These expression vectors were then transiently expressed in neuroblastoma cells (N2a cells) and subsequently infected with 10% brain homogenates from experimentally scrapie-infected mice.

After 4 days of incubation, appearance of newly formed prions can be seen after cell lysis, proteinase-digestion and immunoblot. The blot was developed using 3F4 (which specifically detects the MHM2 construct) as the primary antibody, and detection was carried out using the ECL system. De novo formed prions can be distinguished from residual prions of the inoculate by an epitope-tagging of the under-glycosylated, transfected PrP.

The proteinase K-resistant fragment of $PrP^{Sc}$ was found in cultures expressing the glycosylation mutant and exposed to homogenates from mice infected with three different prion strains: RML, ME7 and 301V(B). Conversion of unglycosylated PrP was blocked by the Q218K mutation. The results showed that all strains of mouse prions tested can convert unglycosylated PrP into prions. No protease-resistant PrP was seen when cells were incubated with no brain homogenates or those from normal mice (CD-1).

When cells were transiently transfected with pSPOX MHM2-PrP (N180Q, N196Q; Q218K), and incubated with a 10% RML mouse-scrapie brain homogenate, no conversion to protease-resistance was seen; this additional mutation at the C-terminus is thought to block an essential conversion co-factor, protein X. The effect of the additional Q218K mutation demonstrates that conversion of under-glycosylated PrP is performed as for wild-type PrP with the help of co-factors, and not a metastability of conformation or a protease-resistance caused by binding of inoculum-derived $PrP^{Sc}$ to under-glycosylated PrP.

When cells were transiently transfected with pSPOX MHM2-PrP wild-type and incubated with a 10% RML mouse-scrapie brain homogenate, almost no protease-resistant PrP could be seen. One very faint band seems to show up at the height of the under-glycosylated PrP, demonstrating that from the different glycoforms of wild-type PrP, it is also the under-glycosylated form that is (although far less efficiently) converted.

These experiments show that prions can be rapidly replicated and amplified in a cell culture system and used to amplify trace amounts of prions in suspected tissues.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claim is:

1. An essay, comprising the steps of:

contacting a sample putatively comprising prions with recombinant neuroblastoma cells (N2a cells), wherein the N2a cells comprise an operative pSOX pSPOX expression vecter comprising an exogenous PrP gene mutagenesized to contain a double mutation where two glycosylation sites are substituted from asparagene to glutamine (N180Q/N196Q) to allow prion infection, and determining the presence of prions in the sample after incubation of the N2a cells with the sample and contacting with 3F4 antibody.

* * * * *

UNITED STATES PATENT AND TRADEMARK OFFICE

CERTIFICATE OF CORRECTION

PATENT NO. : 6,767,712 B2
DATED : July 27, 2004
INVENTOR(S) : Stanley B. Prusiner et al.

It is certified that error appears in the above-identified patent and that said Letters Patent is hereby corrected as shown below:

Column 24,
Line 6, the word "pSOX" after the word "operative" and before the word "pSPOX" should be removed.

Signed and Sealed this

Seventh Day of December, 2004

JON W. DUDAS
*Director of the United States Patent and Trademark Office*